United States Patent
Wenzel et al.

(10) Patent No.: US 9,053,213 B2
(45) Date of Patent: Jun. 9, 2015

(54) INTERACTIVE OPTIMIZATION OF SCAN DATABASES FOR STATISTICAL TESTING

(71) Applicant: KONINKLIJKE PHILIPS N.V., Eindhoven (NL)

(72) Inventors: Fabian Wenzel, Hamburg (DE); Frank Olaf Thiele, Aachen (DE); Stewart Young, Hamburg (DE)

(73) Assignee: Koninklijke Philps N.V., Eindhoven (NL)

( * ) Notice: Subject to any disclaimer, the term of this patent is extended or adjusted under 35 U.S.C. 154(b) by 0 days.

(21) Appl. No.: 14/373,914

(22) PCT Filed: Jan. 15, 2013

(86) PCT No.: PCT/IB2013/050361
§ 371 (c)(1),
(2) Date: Jul. 23, 2014

(87) PCT Pub. No.: WO2013/118001
PCT Pub. Date: Aug. 15, 2013

(65) Prior Publication Data
US 2015/0036948 A1 Feb. 5, 2015

Related U.S. Application Data

(60) Provisional application No. 61/595,851, filed on Feb. 7, 2012.

(51) Int. Cl.
*G06K 9/54* (2006.01)
*G06F 19/00* (2011.01)
(Continued)

(52) U.S. Cl.
CPC ........ *G06F 19/321* (2013.01); *G06F 17/30091* (2013.01); *G06F 17/30247* (2013.01); *G06F 17/3053* (2013.01); *G06T 7/0014* (2013.01); *G06T 2207/30168* (2013.01)

(58) Field of Classification Search
USPC ............... 382/128, 115, 270, 305; 250/208.1; 257/E23.101; 345/419, 420; 438/142; 703/1; 705/1.1, 2, 3, 7.38, 401; 600/475, 306
See application file for complete search history.

(56) References Cited

U.S. PATENT DOCUMENTS 6,954,729 B2 * 10/2005 Lee et al. ........................ 705/1.1
7,428,323 B2 9/2008 Hillman
(Continued)

OTHER PUBLICATIONS

AutoQUANT; Philips; Chapter 6-Managing Databases; webpage: http://www.healthcare.philips.com/main/products/nuclearmedicine/products/workflow/nmapplications/autoquant.wpd.
(Continued)

*Primary Examiner* — Anh Do

(57) ABSTRACT

Generating a patient image collective (34) includes receiving a plurality of candidate images (20) and associated data. At least one inclusion/exclusion rule (44) is applied to the plurality of candidate images and associated data which results in subsets of candidate images (32). The candidate images are tested which result in at least one quality measure (40). The at least one quality measure (40) and associated candidate images are reviewed. The at least one inclusion/exclusion rule (44) is refined based on the reviewed at least one quality measure (40) by at least one of: adding a rule, modifying a rule, deleting a rule, removing a candidate image; and adding a candidate image. The steps of applying the at least one inclusion/exclusion rule through refining the at least one inclusion/exclusion rule are repeated until an optimized collective of images is generated based on a collective size and the at least one quality measure (40). The generated collective is outputted to a data store (34).

20 Claims, 8 Drawing Sheets

(51) Int. Cl.
*G06F 17/30* (2006.01)
*G06T 7/00* (2006.01)

(56) References Cited

U.S. PATENT DOCUMENTS

| | | | |
|---|---|---|---|
| 8,463,006 B2* | 6/2013 | Prokoski | 382/128 |
| 8,494,227 B2* | 7/2013 | Prokoski | 382/115 |
| 2005/0273007 A1 | 12/2005 | Burbar | |
| 2006/0120584 A1 | 6/2006 | Hillman | |
| 2008/0037876 A1 | 2/2008 | Galperin | |
| 2010/0074480 A1 | 3/2010 | Minoshima et al. | |
| 2010/0152577 A1 | 6/2010 | Young et al. | |

OTHER PUBLICATIONS

Chen, W. P., et al.; Effect of sample size for normal database on diagnostic performance of brain FDG PET for the detection of Alzheimer's disease using automated image analysis; 2008; Nucl. Med. Commun.; 9:837.

Hattori, N., et al.; Diagnostic Z-score mapping: Use of younger normal database to improve discrimination of dementia; 2008; Journal of Nuclear Medicine; 49 (Supplement 1); 5P.

Hwang, J. H., et al.; Gender differences in age-related decline of regional cerebral glucose metabolism; 2008; Journal of Nuclear Medicine; 49 (Supplement 1); 36P.

Ishii, K., et al.; Computer-assisted diagnostic system for neurodegenerative dementia using brain SPECT and 3D-SSP; 2009; Eur. J. Nucl. Med. Mol. Imaging; (5)831-840.

Schmidt, J., et al.; Interpreting PET Scans by Structured Patient Data: A Data Mining Case Study in Dementia Research; 2010; Kowl. Inf. Syst.; 24:149-170.

Varrone, A., et al.; EANM procedure guidelines for PET brain imaging using [18F]FDG, version 2; 2009; European Journal of Nuclear Medicine and Molecular Imaging; 36(12)2103-2110.

Waxman, A. D., et al.; Society of Nuclear Medicine Procedure Guideline for FDG PET Brain Imaging; 2009; Citeseer; pp. 1-12.

Wenzel, F., et al.; B-spline-based stereotactical normalization of brain FDG PET scans in suspected neurodegenerative disease: Impact on voxel-based statistical single-subject analysis; 2009; Neuroimage; 50(3) 994-1003.

Zhang, W., et al.; Registration of Unseen Images Based on the Generative Manifold Modeling of Variations of Appearance and Anatomical Shape in Brain Population; 2012; Mathematical Methods in Biomedical Image Analysis; IEEE Workshop; pp. 113-118.

* cited by examiner

INTERACTIVE OPTIMIZATION OF SCAN DATABASES FOR STATISTICAL TESTING

CROSS REFERENCE TO RELATED APPLICATIONS

This application is a national filing of PCT application Serial No. PCT/IB2013/050361, filed Jan. 15, 2013, published as WO 2013/118001 A1 on Aug. 15, 2013, which claims the benefit of U.S. provisional application Ser. No. 61/595,851 filed Feb. 7, 2012, which is incorporated herein by reference.

The present application relates generally to medical imaging. It finds particular application in conjunction with generating and maintaining databases of nominal reference images, and will be described with particular reference thereto. However, it will be understood that it also finds application in other usage scenarios and is not necessarily limited to the aforementioned application.

One technique for interpreting a scanned patient image is comparing it with a nominal reference images. Reference images are generated from patient populations which are considered normal. Evaluating the scanned patient image using the reference images is increasing done through voxel-wise statistical testing in medical domains such as neurology and cardiology. Images are fitted or warped to an anatomical template and individual voxels are compared. Voxel-wise statistical testing determines the differences between an individual image and a range of variation in a set of reference images.

Choosing a set of reference images or collective which represent a normal population should cover the variability of healthy subjects in order to provide a more accurate clinical interpretation. Selection of images for a normal collective representing the normal population should not be biased by co-variability. For example, if the normal collective of reference images only included images of young patients, then age affects such as increased heart ventricles, or reduced global metabolic activity would incorrectly indicate abnormalities in a normal older patient otherwise healthy.

A normal collective of images are available from many sources. However, variations in local imaging implementations show that the normal collective may not represent a collective best suited for a specific implementation of an imaging device or a medical facility. Local variations in imaging are reflected in clinical protocols and technical parameters used in imaging such as reconstruction algorithms employed, post-processing filters applied, patient attenuation corrections made using a specific device at a specific location. Differences can be found in the patient imaging environment such as area lighting and protocol variation which are reflected in patient images. The differences reflected in patient images affect the voxel-wise testing in comparing a locally scanned patient image with the collective.

Although generally suggested that local variations exist and healthcare practitioners need to review and revise the collective of scanned images to include local variations, methods and support to do so have been absent. Furthermore, new protocols and techniques are constantly being introduced which impact the time and ability of local imaging sites to incorporate and manage the on-going changes to their local collectives. The normal collective should not be one fixed set of references images, but optimally, an evolving set of images which reflect the type of device used, the imaging technique employed, patient characteristics relevant to a normal representation, and local variations. The type of device type, the image type, the manufacturer, and the like. The imaging technique includes a used includes the device protocol used, an isotope used, a CT or MRI contrast agent used, and the like. The relevant patient characteristics vary depending upon the protocol, but can include age, ethnicity, sex and the like. Relevant patient characteristics can include information from other examinations.

The present application discloses a new and improved interactive optimization of a image collective which addresses the above referenced matters, and others.

In accordance with another aspect, an imaging system which generates a patient image collective includes a data store, and one or more processors. The data store stores a collective of images. The one or more processors are programmed to receive a plurality of candidate images and associated data for inclusion in the collective of images. The one or more processors apply at least one inclusion/exclusion rule to the plurality of candidate images and associated data which results in an subset of candidate images. The one or more processors test the candidate images based on at least one quality measure. The one or more processors review the at least one quality measure and the candidate images and refine the at least one inclusion/exclusion rule based on the reviewed at least one quality measure by at least one of: adding a rule, modifying a rule, deleting a rule, removing a candidate image; and adding a candidate image. The one or more processors repeat the steps beginning with applying at least one inclusion/exclusion rule until an optimized collective of images is generated based on the collective size and reviewed at least one quality measure. The one or more processors output at least one generated collective to the data store or to a display.

In accordance with one aspect, a method for generating a patient image collective includes receiving a plurality of candidate images and associated data. At least one inclusion/exclusion rule is applied to the plurality of candidate images and associated data which results in a subset of candidate images. The candidate images are tested based on at least one quality measure. The at least one quality measure and the candidate images are reviewed. The at least one inclusion/exclusion rule is refined based on the reviewed at least one quality measure by at least one of: adding a rule, modifying a rule, deleting a rule, removing a candidate image; and adding a candidate image. The steps of applying the at least one inclusion/exclusion rule through refining the at least one inclusion/exclusion rule are repeated until an optimized collective of images is generated based on a collective size and the at least one quality measure. The generated collective is outputted to a data store or to a display.

In accordance with another aspect, an imaging system includes a data store and one or more processors. The data store stores an image collective in a common space. The one or more processors are configured to receive candidate images, transform the candidate images to common space, retrieve the image collective from the data store and refine the image collective by adding candidate images to the image collective and excluding images from the image collective by applying rules and or quality measures based on: (i) individual image characteristics, (ii) available information about patients and patient histories, and (iii) clinical information from other medical examinations.

One advantage is a collective can be adapted to locality quickly and efficiently.

Another advantage resides in healthcare practitioners interactively defining a local collective.

Another advantage resides is that healthcare providers can localize collectives to specific sites or implementations.

Still further advantages of the present application will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates the current use of a collective in voxel-wise statistical testing.

FIG. 2 diagrammatically illustrates one embodiment of the system which generates a collective.

Figure 6:
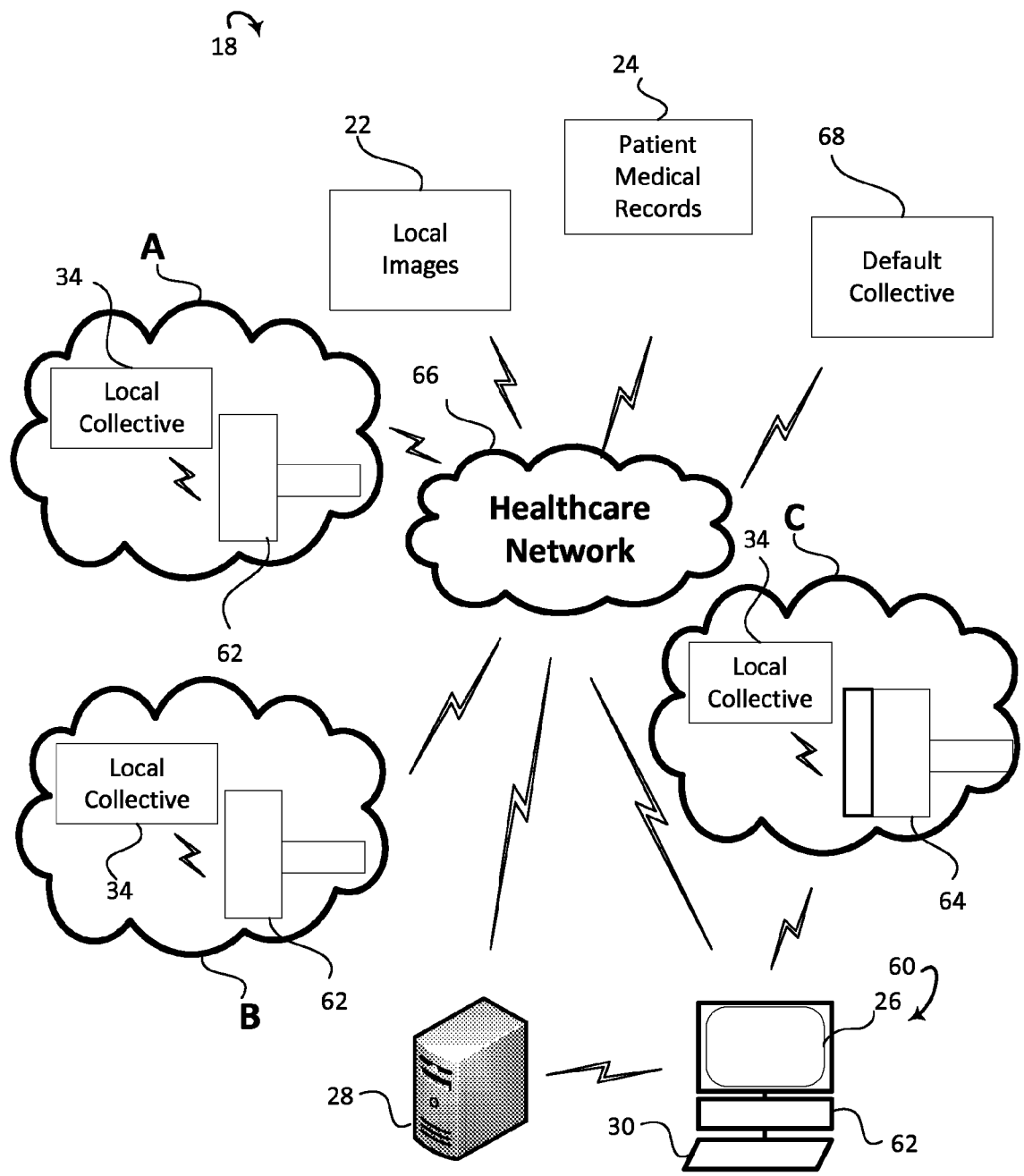

FIG. 6 schematically illustrates one embodiment of the system in a healthcare provider environment.

Figure 7:
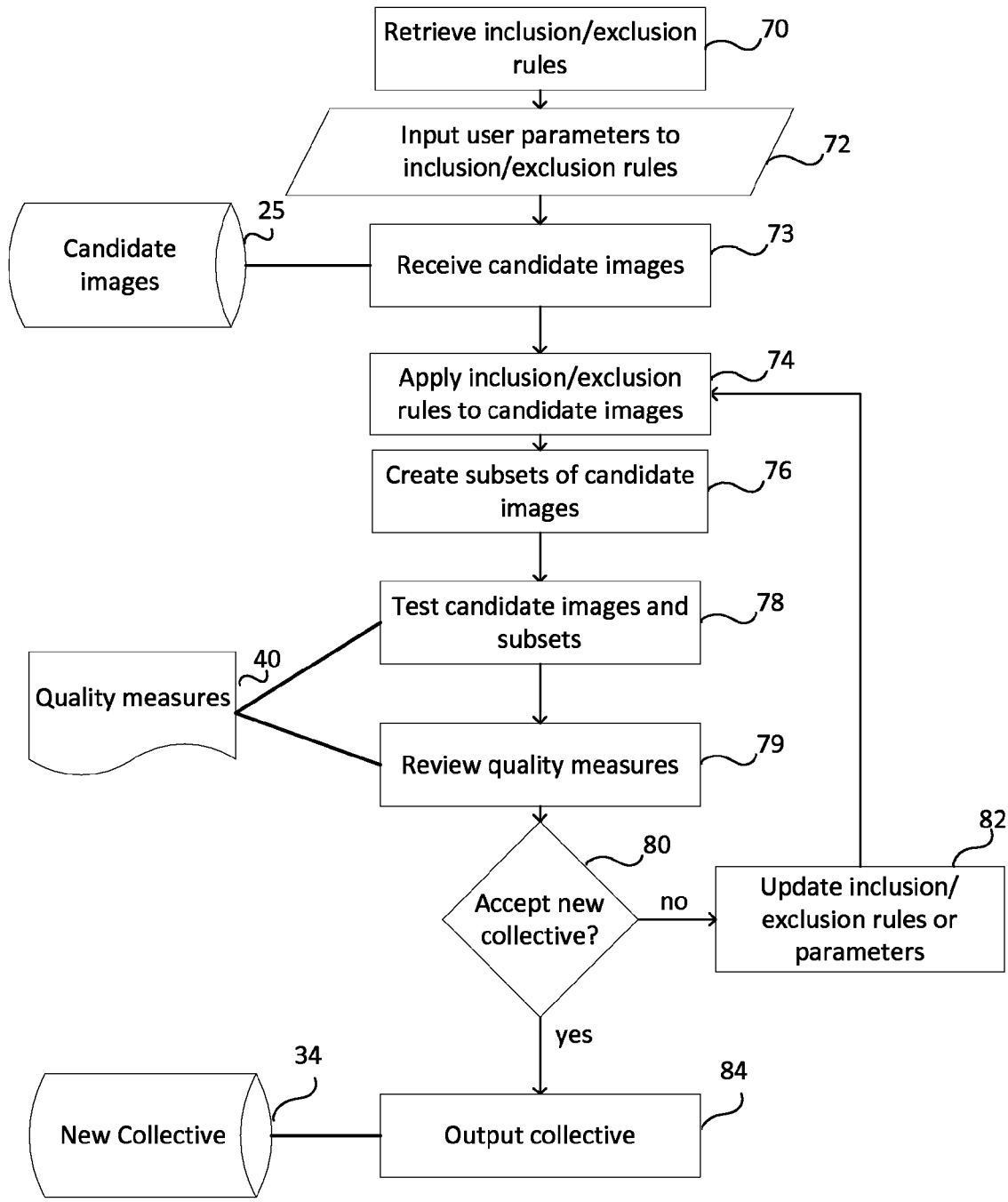

FIG. 7 flowcharts one embodiment of generating a collective.

Figure 8:
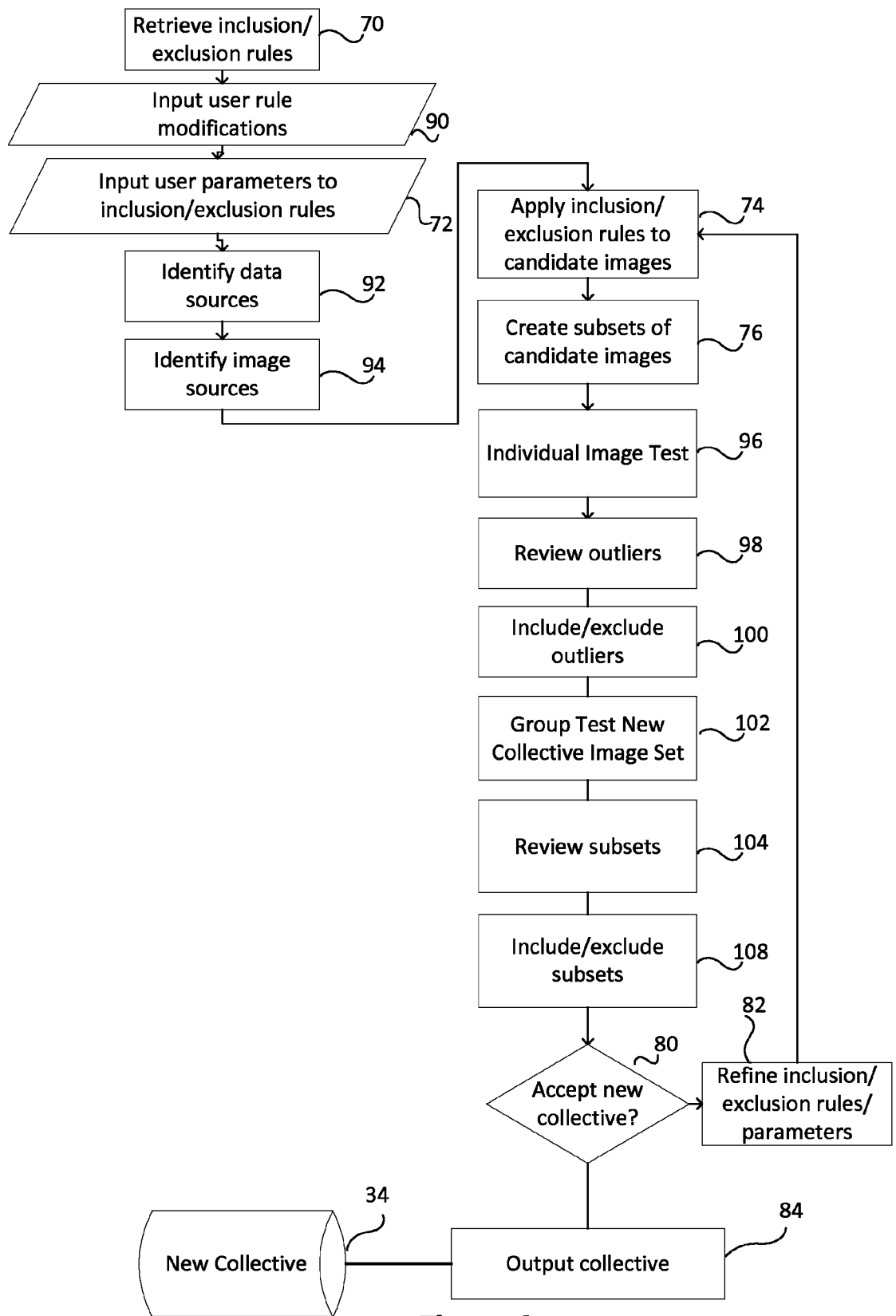

FIG. 8 flowcharts another embodiment of generating a collective.

Figure 1:
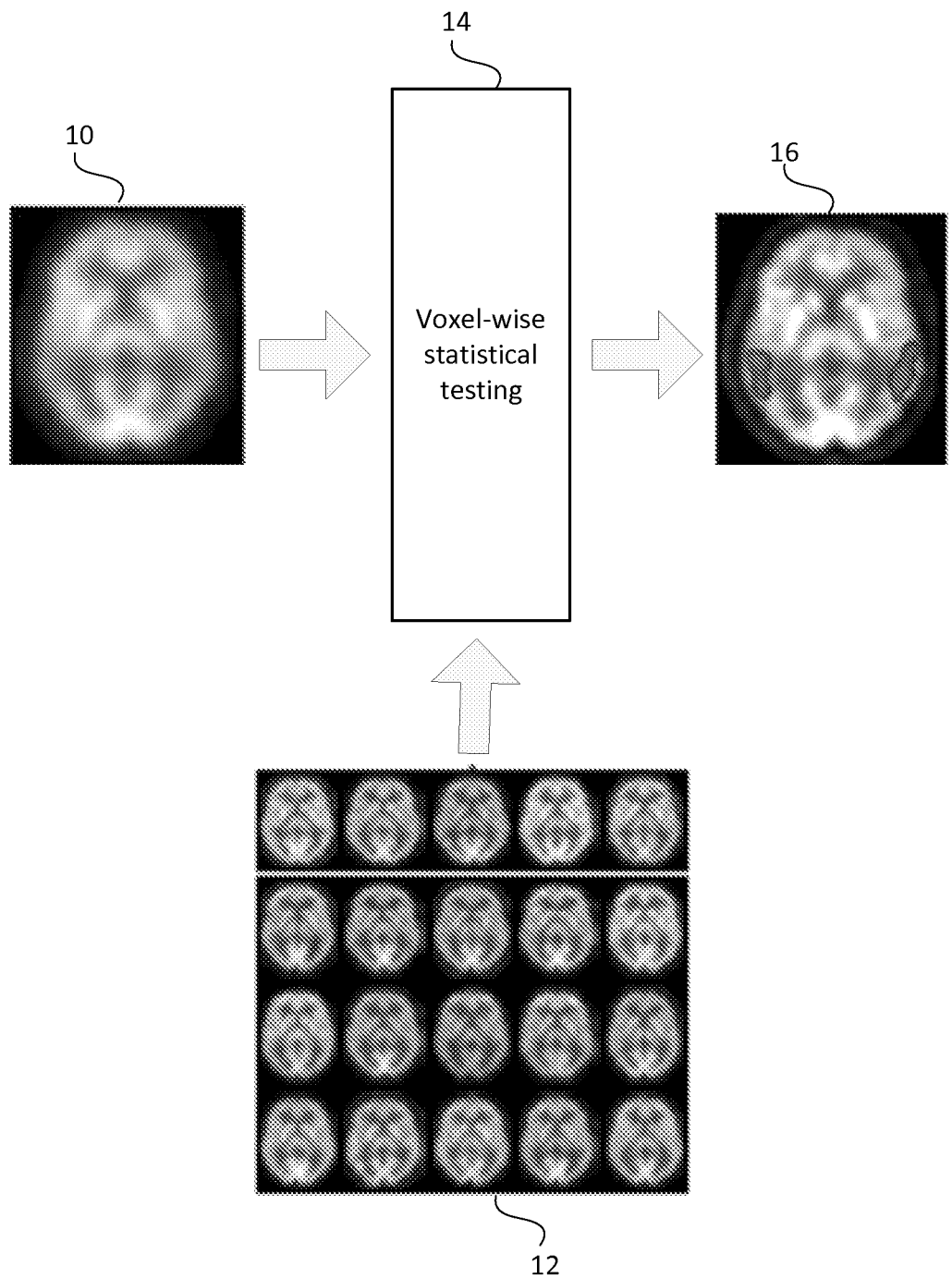

With reference to FIG. 1, the current use of a collective in voxel-wise statistical testing is schematically illustrated. A patient image 10 is generated from a scanner.

The patient image is smoothed and then transformed to a common space defined by a template. The patient image 10 is compared with a normal collective 12, which represents a variability of normal patients using voxel-wise statistical testing 14. The images in the collective 12 have also been smoothed and transformed to the common space. The image 10 and/or collective 12 are typically stored in a database of a system such as a Hospital Information Support System (HISS), a Picture Archive and Communication System (PACS), a Radiology Information System (RIS), a Clinical Decision Support System (CDS) or the like. The collective can include images based on the medical literature, actual patient studies, and the like, which represent a normal population for various imaging protocols.

Voxel-wise statistical testing 14 is well known in the art. The intensity of individual voxels of the patient image are compared with the images of the normal collective 12. The collective 12 includes a distribution of intensities for each voxel in the common space. By comparing the individual voxels of the image 10 with the collective 12, what is different from normal is determined by variance to the statistical distribution of intensities of the collective 12. A statistical probability is determined if the individual voxel is different from the collective. The probabilities for all voxels comprise a statistical map 16 which is used to represent visually the abnormal areas of the patient image through differences in color, grey scale, cross hatching, or the like on a display.

Figure 2:
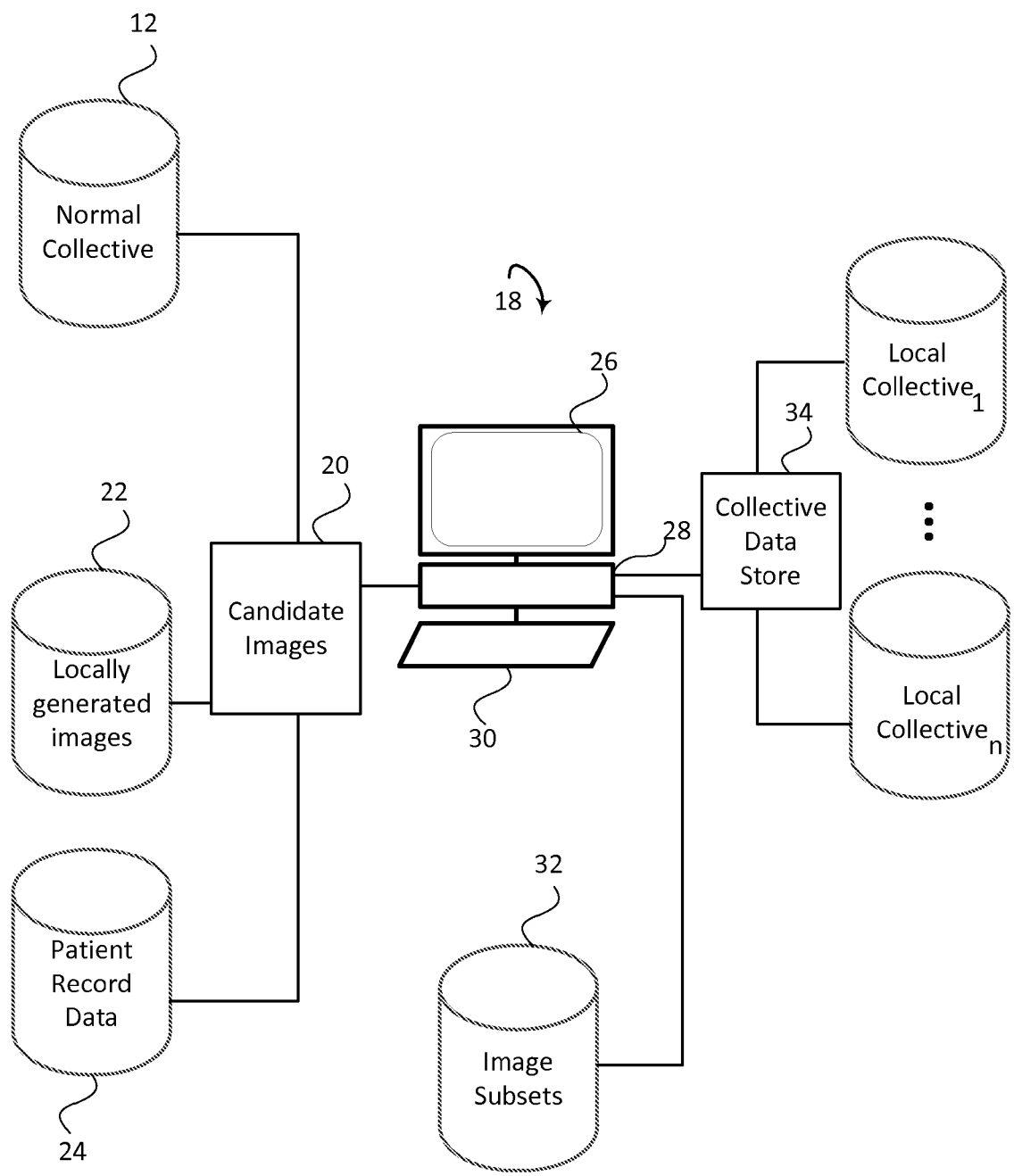

FIG. 2 diagrammatically illustrates one embodiment of a system 18 which generates or maintains the collective. Candidate images 25 for the collective 20 are retrieved from a variety of sources such as a normal collective 12 delivered with a scanner, downloaded from a website, or the like, and locally generated images 22. The locally generated images 22 can be stored in a local database or in a database as part of a larger system such as a HISS, PACS, RIS, CDS, and the like. Retrieval can be at the object or database level, system level, or network level. Retrieval includes retrieving the image and the image attributes. The image and attributes can be in a standard format such as Digitial Imaging and Communications (DICOM). The DICOM standard defines hundreds of possible attributes for an image. Additional information about the patients represented in the images can be retrieved from a patient medical record database 24 which includes clinical information from other examinations. For example, a source of candidate images can include an initial search for images of patients having the highest normal score in a neuro-psychological test such as MMSE. Alternatively if medical record information is inaccessible, a checklist can be provided to the healthcare practitioner to verify that the particular image meets candidate criteria.

Figure 3:
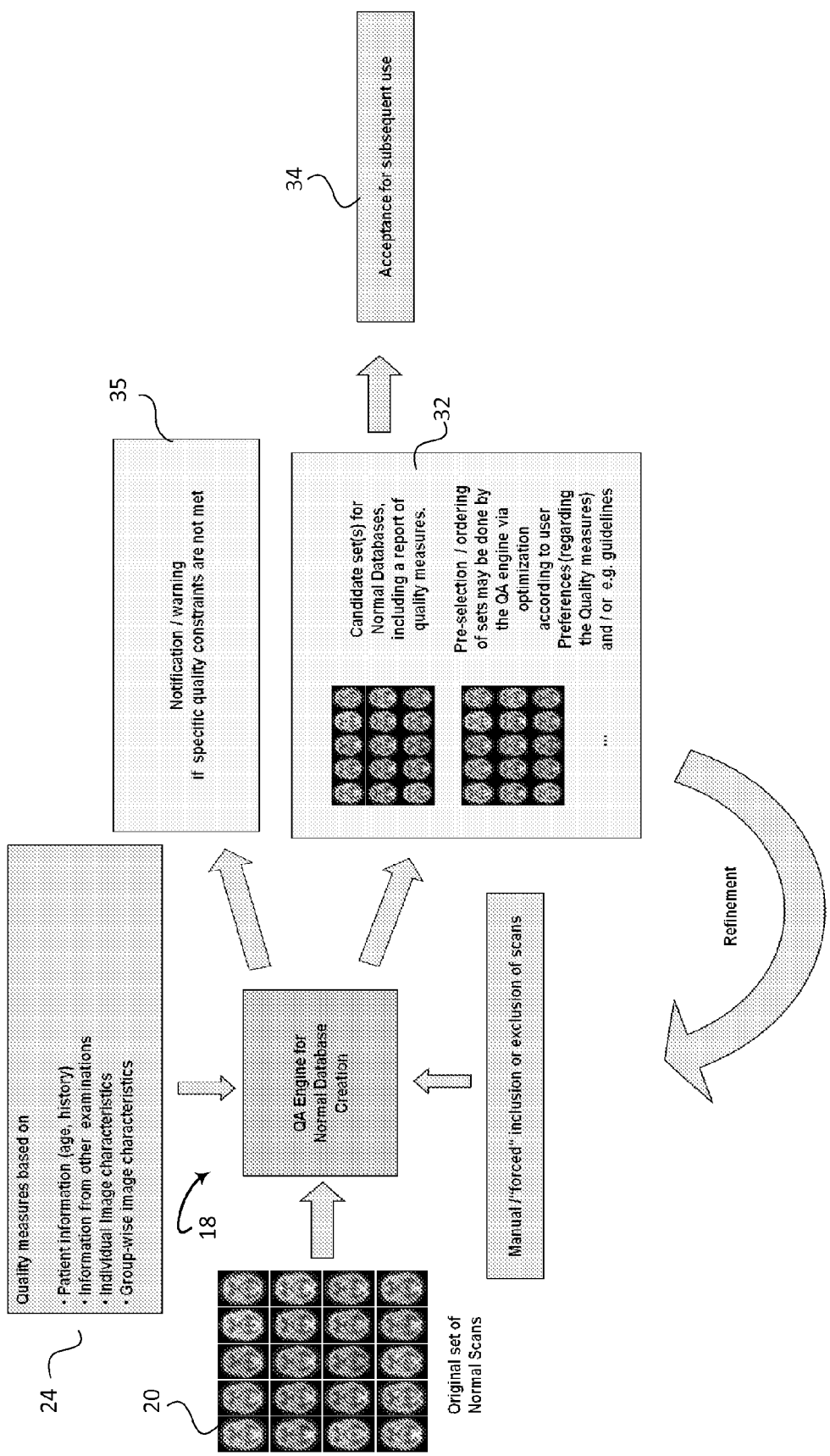
FIG. 3 illustrates one embodiment of the system which through a quality assurance engine iteratively defines a collective.

FIG. 3 illustrates one embodiment of the system which through a quality assurance engine iteratively defines a collective. The system 18 processes the candidate images iteratively, refining the collection of patient images according to a set of rules and measurements which result in a reference collective of patient images 34. An example of a rule is to include 20 images of patients with the highest normal score in a neuro-psychological exam such as MMSE. This is an alternative to defining the candidate images by the data source. Processing is by one or more processors 28 which test the images and provide measurements which indicate whether an image or a subset of images should be included in or excluded from the collective 34. Interaction with a healthcare practitioner occurs through a display device 26 and one or more input devices 30 such as a keyboard or a mouse. The iterative process includes subsetting the candidate images and ordering them for inclusion in the collective. The subsetted images 32 can be stored locally as needed for review by the healthcare practitioner. Quality measurements are provided which test individual images and subsets of images for inclusion or exclusion.

The iterative process outputs one or more collectives in a data store. The data store defines the local collective of images 34. The images define by the local collective 34 can be stored locally, or separately with a local pointer to the remote object. Multiple local collectives include individual collectives defined by a normal population for a particular usage such as the particular protocol followed, the isotope used, reconstruction algorithms employed, post-processing filters applied, attenuation corrections, patient characteristic and the like. An image can participate in multiple local collectives if it meets the necessary criteria established for inclusion in each collective. The healthcare practitioner can review a proposed local collective which is output by the system or in one embodiment can interactively review each step. The healthcare practitioner can review related quality measures with each image such as patient historical data, data from other examinations, other patient images such as from other modalities and the like. Warnings or notices 35 are displayed if a quality measure is not met.

Figure 4:
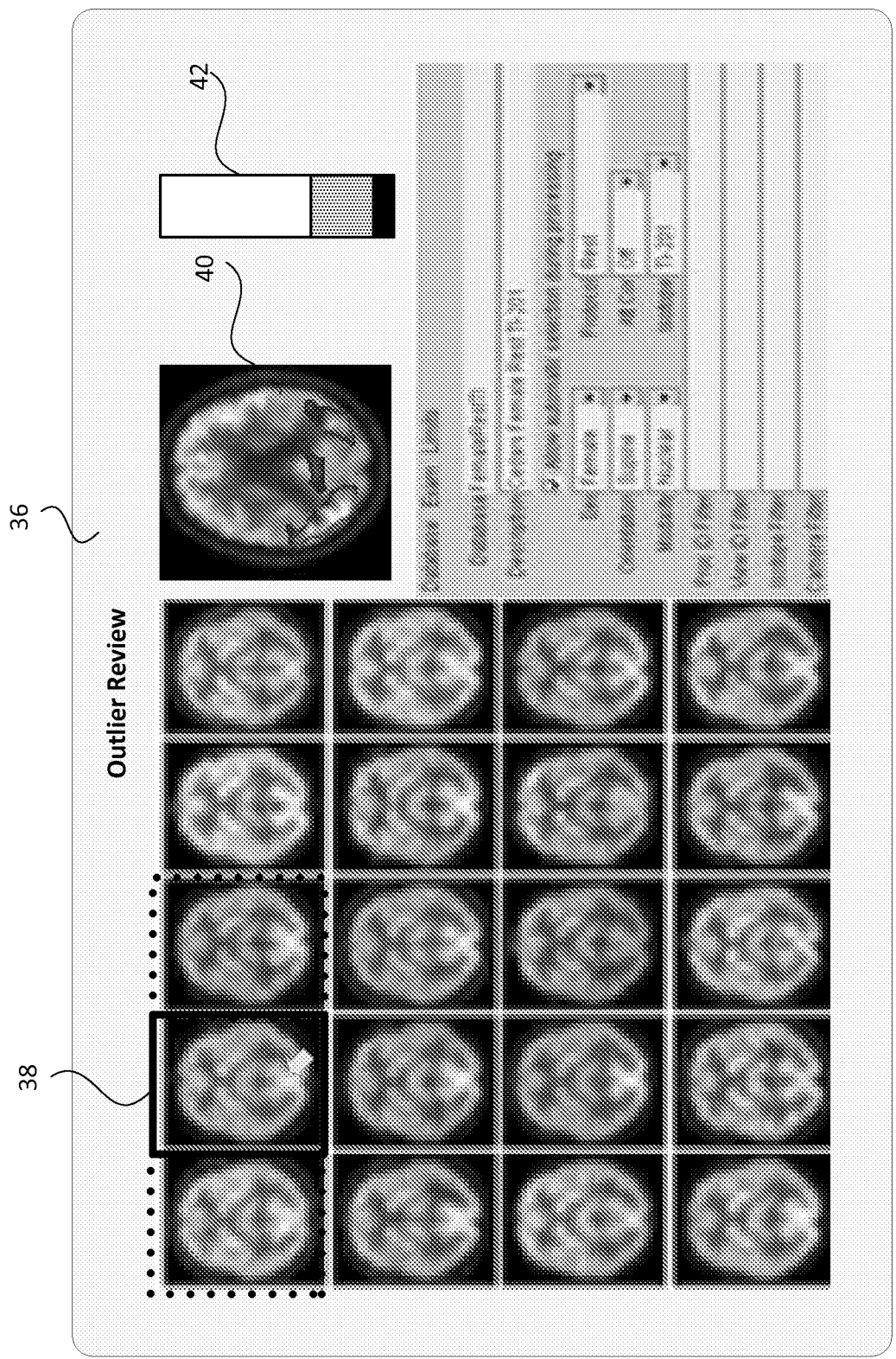
FIG. 4 illustrates one embodiment of a display for interactive review for outlier images.

FIG. 4 illustrates one embodiment of a display 36 for interactive review for outlier images. The candidate images for the collective can be tested for outliers using a quality measurement such as a leave one out test which measures variance from other candidate images. An example is to statistically compare each voxel of a candidate image with the voxels of the remaining candidate images. A threshold amount or variance indicates a outlier. The variance for the entire image 38 can be shown using a quality measure 40 such highlighted or colored pixels exceeding the threshold, or a statistical polar plot, a bar chart, etc. Statistical polar plots are particularly applicable to cardiac images. The quality measure can be shown for each image. The system 18 indicates whether each image is an outlier image 38 based on a variance from all images or images within a subset according to a volume of voxels which exceed a threshold amount of significantly abnormal metabolism, a percentage of the volume which exceeds a threshold amount, or the like. The volume can include the entire image or a portion of the image such as a region of interest or an anatomical feature. The images can be sorted in order by the amount or percentage exceeding a threshold. Another quality measure 42 that includes a reference of the average over all other images of the volume exceeding the threshold can be provided with the volume for the particular image. In the example display, the dark bottom bar represents the average total volume of all candidate images except the one image. The shaded bar represents the volume of the one image which exceeds thresholds. Exclusion of the image as an outlier removes the image as a candidate for the collective. Exclusion can be accomplished by removing by image from the candidate images considered or by the addition of a rule which excludes the particular image.

The display 36 of the candidate outliers 38 for review is, in some embodiments, reviewed by a healthcare practitioner. Alternatively, the outliers 38 can also be excluded automatically through thresholding. The alternate embodiment reduces or eliminates time by the healthcare practitioner for review of individual images.

Figure 5:
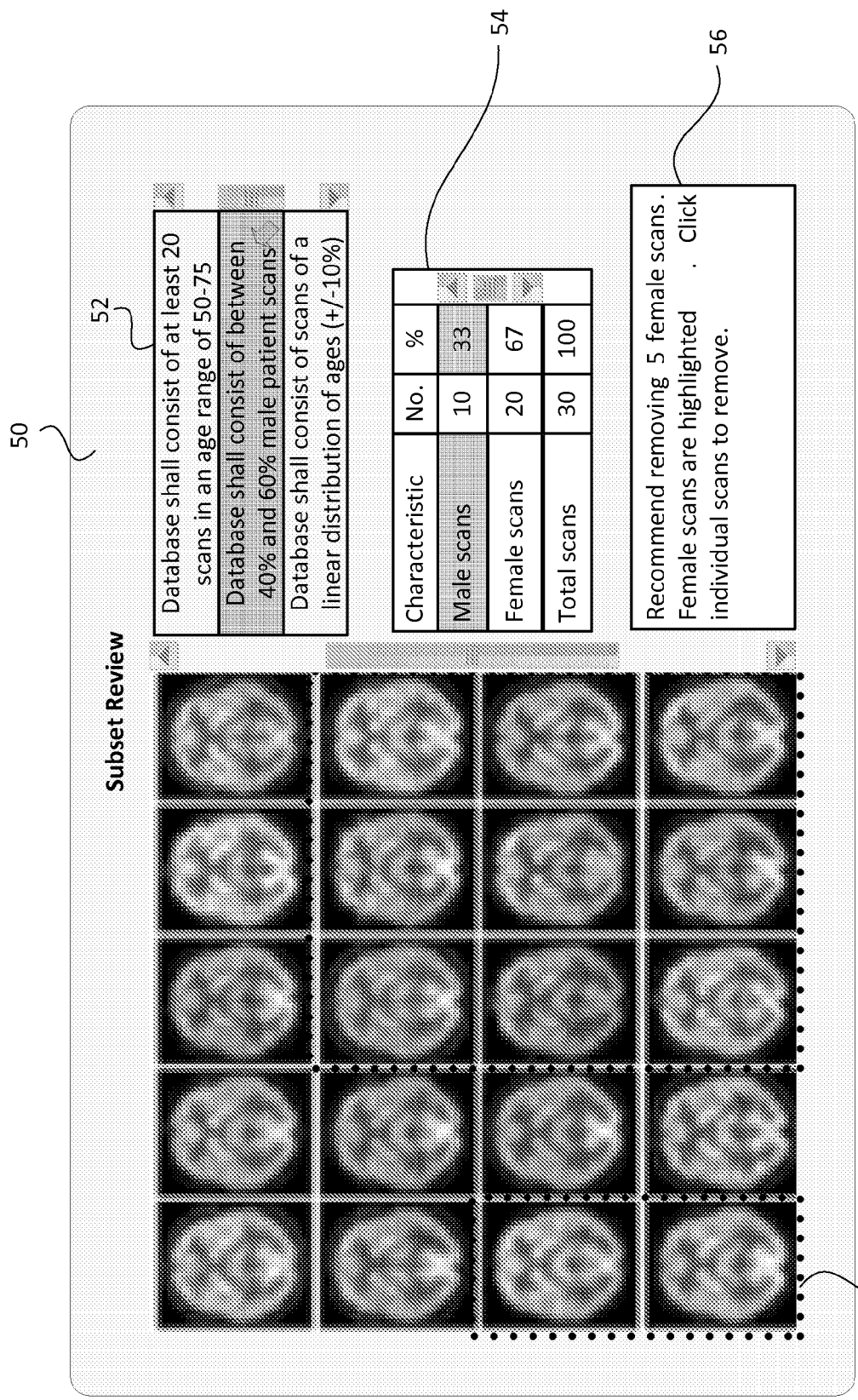
FIG. 5 illustrates one embodiment of a display for interactive review of subsets of images.

FIG. 5 illustrates one embodiment of a display 50 for interactive review of subsets. A second type of test includes a subset review of subsets 32 of candidate images and associated quality measures. Subsets are based on rules 52 for inclusion and/or exclusion. Examples of rules include that the collective shall include at least 20 images in an age range of 50-75; the collective shall include between 40-60% male patient images; the collective shall include between 20-30 total images; the collective shall include a linear distribution of ages (±10%); etc. In the display, an example of the rule whereby the collective shall include between 40-60% male patient images shows where the candidate images do not meet the rule. There are currently 10 male images and 20 female images where the percentage of male images is 33%, below the 40% minimum set by the rule.

One of the rules 52 is highlighted and a quality measure 54 such as the percentage distribution of images in the target population is shown. Additional quality measures include analysis of variance (ANOVA), descriptive statistics, and the like. Warnings and/or notice are provided where rule constraints are not met such as by hightlighting a rule, highlighting the subset of images, giving a written explanation, and the like. The quality measures include statistical measures expressed as numbers or graphically such as polar plots, bar charts, pie charts, and the like. Statistical measures can include the intensity distribution in the subset of images and/or include patient characteristics obtained from the image attributes or from the patient medical record. Refinement of which candidates are further included are based on the quality measures. Another quality measure compares the voxel-wise distribution of candidate images with a maximum range to ensure sensitivity to a variation from normal or to ensure intensity scaling permits testing of abnormal conditions. In another embodiment, synthetic lesions are added to one or more images and a quality measure includes the extent to which voxel-wise testing is able to detect the lesions.

Optionally a recommendation 56 is provided to the healthcare practitioner to interactively amend the subsets by included other images and/or excluded current images. In the example display, a recommendation is provided to remove 5 female images which increases the percentage of male images to meet the rule of between 40-60% male images.

FIG. 6 schematically illustrates one embodiment of the system 18 in a healthcare provider environment. The healthcare practitioner interacts with the system 18 to define one or more local collectives using a workstation 60. In the example shown, the healthcare provider includes scanners 62 such as a MRI, a PET, a SPECT, and combination scanners at multiple locations such as A, B, and C. The same scanner model is found at several locations, e.g. locations A and B. A similar, but different scanner model 64 is found at a location C. The environment characteristics such as lighting and protocol variations are most similar between two locations which have possibly somewhat different, but comparable scanner models, B and C. The local collectives 34 at each locality are defined using the system 18 and the images from each of the locations. The local collectives 34, the scanners 62, 64, the medical record database 24, the locally generated images 22, are accessible through a network 66. The collectives can also include a default collective 68, and the like, which initially can be delivered with one of the scanners.

The default collective 68 serves as the starting point which is customized to healthcare provider protocols, patient protocols, etc. As new protocols are developed, new images are added to and/or original images are removed from the default collective 68. The local scanners 62, 64 use the default collective 68 for the new protocol, and as more local images are created, the local collective 34 particular to that scanner or location can be generated. The local collective 34 can weight the rules for inclusion of particular subsets of images where the default collective is given less weight, and the locally generated images 22 the most weight for inclusion. Depending upon the volume of images locally generated, and a frequency the local collective is revised, the local collective 34 will initially reflect the default collective 68, but over time will come to reflect more and more the locally generated images.

Similarly, a new installation of a scanner at a healthcare provider can also draw candidate images from other local collectives 34 which use the same scanner model by including the candidate images in the image sources and weighting rules for image inclusion. Additionally, environmental factors can be considered in the iterative process. Candidate images from comparable scanners which share common environmental factors can be included by including the candidate images from the image sources and weighting rules for image inclusion. In establishing a new local collective 34, images can be draw from multiple sources with weighting applied to select the most beneficial images for the new local collective. The local collective can continue to add and expand using the experiences of the healthcare provider in general, and the specific experiences of selected localities.

FIG. 7 flowcharts one embodiment of generating the local collective 34. One embodiment uses a iterative process which inputs the delivered or default collective 68, and the candidate local images 22 and generates a proposed local collective which is then accepted or modified by the healthcare practitioner.

In a step 70, the rules 52 for image inclusion/exclusion are retrieved by the system 18. In one embodiment the rules are transparent to the healthcare practitioner. The system uses input of user parameters in a step 72, obtained from the healthcare practitioner, to select candidate images for inclusion. The user parameters include specific attributes or patient characteristics frequently defined by a protocol. User parameters can also include the sizing of the collective, or weighting of input sources.

The rules for inclusion/exclusion 52 are applied to the candidate images 22 in a step 74. Some of the candidate images are excluded in exclusion rules according to image attributes or other data sources. Some of the candidate images are included which have data attributes or other patient data characteristics for inclusion. The rules and candidate images can be treated as an optimization problem by finding the best collective among possible choices of candidate images, associated data and data attributes.

In a next step 76, the result set is sorted into subsets according to satisfying the constraints imposed by the rules. The subsets allow grouping of images according to common characteristics which satisfy one or more rule constraints. For example, the highest subset includes only the images which satisfy all rules. The next subset satisfies most, but not all rules. In the example from FIG. 5, the images of males will satisfy the rules, if images of 5 female images are removed. In subsets, the subset of images of males are before the images of females.

Various tests are applied in a step 78, to the candidate images and the subsets of images in the result set to test compliance with the quality measures. The quality measures include quality measures on individual images such as the outlier testing discussed with reference to FIG. 4. The quality measures include quality measures for subsets such as the subset testing discussed with reference to FIG. 5. The quality measures can include measures of overall image quality, image distribution of voxel intensities overall or in specific areas, and the like. The quality measures can include statistical measurements of patient data, other test results, other conditions, and the like.

The proposed collective is reviewed for acceptance in a step 80. Based on the quality measures, a number of candidate images, and a target size of the proposed collective, and the like, additional iterations are performed. If another iteration is performed either to reduce the size of the proposed collective, to exclude candidate images based on the quality measures, or the like, then the rules are revised in a step 82 and another iteration of the process is performed beginning with applying the revised inclusion/exclusion rules to the current result set.

If the proposed collective is accepted, then it is output in a step 84. The output of the proposed collective can include an optional review of the new collective by the heathcare practitioner. The new collective is output to a data store which defines the collective 34. The images can be stored with the definition of the collective or only as a reference to the images which are stored in a system such as a HISS, PACS, RIS, CDS or the like. The new collective is available for voxel-wise statistical testing as discussed with reference to FIG. 1.

FIG. 8 flowcharts another embodiment of generating a collective. This embodiment and variations expands upon the method of FIG. 7 with optional steps. In an optional step 90, the healthcare practitioner can add, modify, and delete rules. The system provides default and model rules which are further refined according to the needs of the healthcare practitioner.

In another optional step 92, the identities of data sources are input. The data sources include patient records, nonstandard attributes, and the like which provide further refinement in the collective. Various localities, default collectives, delivered collectives, and the like are made known to the system in a step 94. Weighting of sources can optionally be input for both data sources and for image sources. The integration of data sources can be at the object and/or database level, system level, or network level. The input of the data source identity can include direct entry, browsing or discovery capabilities.

Tests and resulting quality measures are broken out in multiple steps for interactive review by a healthcare practitioner. Tests of individual images such as discussed with reference to FIG. 4 are perform in a step 96. The next step 98, is the display of the quality measures for the individual images such as shown in FIG. 4 for review by a healthcare practitioner. In an optional step not shown, the healthcare practitioner can display the individual image highlighted as a outlier and compare the outlier image with a normative reference or another image to determine whether to include/exclude the outlier image. The healthcare practitioner in a step 100, indicates which outliers are included/excluded by, for example, clicking an image icon.

Similarly group tests are performed such as discussed with reference to FIG. 5 in a step 102. The subsets and quality measures are displayed for review by the healthcare practitioner in a step 104. The healthcare practitioner reviews the list of subsets and can in an optional step drill down into the subset of images for further review and comparison of individual images within the subset or comparison of characteristics of the subset with other subsets. Analogously to the individual image inclusion/exclusion, the healthcare practitioner in a step 108 can indicate which subsets to include/exclude. A subset can be one or more images.

The method has been described in reference to the development of a collective which represents a normal population. The method can also be used to generate a collective which represents an abnormal collective e.g. a specified disease state. This inverts the voxel-wise test from what is different from the normal collective to voxel-wise testing of what is common to the abnormal collective. Wherein the statistical map output of voxel-wise testing in FIG. 1 represents probabilities of individual voxels being different from normal, the statistical map alternatively can represent the probability of being different from the abnormal, or common to the abnormal. The abnormal collective or a series of abnormal collectives can be used in automated diagnosis to determine the presence of a disease and its degree of advancement.

It is to be appreciated that in connection with the particular exemplary embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An imaging system which generates a patient image collective, comprising:
   a data store which stores a collective of images;
   one or more processors programmed to:
   a) receive a plurality of candidate images and associated data for inclusion in the collective of images;
   b) apply at least one inclusion/exclusion rule to the plurality of candidate images and the associated data which results in a subset of candidate images;
   c) test the candidate images based on at least one quality measure;
   d) review the at least one quality measure and the candidate images;
   e) refine the at least one inclusion/exclusion rule based on the reviewed at least one quality measure by at least one of: adding a rule, modifying a rule, deleting a rule, removing a candidate image; and adding a candidate image;
   repeat b)-e) until an optimized collective of images is generated based on the collective size and reviewed at least one quality measure; and
   output at least one generated collective to the data store or to a display.

2. The imaging system which generates the patient image collective according to claim 1, further comprising:
   a workstation including:
   a display connected to one or more processors which displays the at least one quality measure and the candidate images; and
   at least one input device connected to the one or more processors which inputs inclusion/exclusion information from a healthcare practitioner interactively reviewing at least one of the quality measures and the candidate images.

3. The imaging system which generates the patient image collective according to claim 1, wherein the processor is further programmed to:
   transform patient images to a common space; and compare the transformed patient image to the collective of images in a voxel-wise statistical test.

4. The imaging system which generates the patient image collective according to claim 1, wherein the data store includes multiple collectives.

5. The imaging system which generates the patient image collective according to claim 1, wherein the plurality of candidate images include a default collective.

6. The imaging system which generates the patient image collective according to claim 1, wherein the plurality of candidate images include collectives from different localities; and
   wherein the at least one inclusion/exclusion rule includes weighting of the different locality collectives as the candidate images.

7. The imaging system according to claim 1, wherein the image collective is based on local variation.

8. A method for generating a patient image collective, comprising:
   a) receiving a plurality of candidate images and associated data;
   b) applying at least one inclusion/exclusion rule to the plurality of candidate images and the associated data which results in a subset of candidate images;
   c) testing the candidate images based on at least one quality measure;
   d) reviewing the at least one quality measure and the candidate images;
   e) refining the at least one inclusion/exclusion rule based on the reviewed at least one quality measure by at least one of: adding a rule, modifying a rule, deleting a rule, removing a candidate image; and adding a candidate image;
   repeating b)-e) until an optimized collective of images is generated based on a collective size and the at least one quality measure; and
   outputting the generated collective to a data store or to a display.

9. The method for generating the patient image collective according to claim 8, wherein there are a plurality of the inclusion/exclusion rules and further including weighting the inclusion/exclusion rules.

10. The method for generating the patient image collective according to claim 8, wherein the plurality of candidate images and the associated data includes images and data from patient medical records.

11. The method for generating the patient image collective according to claim 8, wherein the at least one quality measure includes an outlier test in which each candidate image is left out as the remaining candidate images are checked for similarity.

12. The method for generating the patient image collective according to claim 8, wherein the at least one quality measure includes a statistical measurement of a voxel-wise subset distribution which identifies subsets of images with distributions exceeding a threshold amount.

13. The method for generating the patient image collective according to claim 8, wherein the reviewing includes generating a visual display of a statistical measurement of candidate image variation.

14. The method for generating the patient image collective according to claim 8, wherein the reviewing includes displaying an image with the image areas highlighted which exceed statistical parameters.

15. The method for generating the patient image collective according to claim 8, wherein the reviewing includes generating a visual display of representations of image subsets and at least one subset measurement.

16. The method for generating the patient image collective according to claim 8, wherein the candidate images are Positron Emission Tomography (PET) brain scans.

17. The method for generating the patient image collective according to claim 8, wherein the refining includes modifying the weight of at least one rule.

18. The method for generating the patient image collective according claim 8, wherein the display of a statistical measurement includes a statistical polar plot.

19. A non-transient computer readable medium carrying software which controls one or more processors to perform the method of claim 8.

20. An imaging system comprising:
   a data store which stores an arcane collective in a common space;
   one or more processors configured to
   receive candidate images,
   transform the candidate images to common space, retrieve the image collective from the data store,
refine the image collective by adding candidate images to the image collective and excluding images from the image collective by applying rules and/or quality measures based on (i) individual image characteristics, (ii) available information about patients and patient histories, (iii) clinical information from other medical examinations.

* * * * *